(12) United States Patent
Hunn

(10) Patent No.: US 10,537,362 B2
(45) Date of Patent: Jan. 21, 2020

(54) DEVICE FOR POSITIONING A PROBE IN LIVING TISSUE

(75) Inventor: Marcel Hunn, Langenthal (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 1927 days.

(21) Appl. No.: 11/868,086

(22) Filed: Oct. 5, 2007

(65) Prior Publication Data

US 2008/0146904 A1 Jun. 19, 2008

Related U.S. Application Data

(63) Continuation of application No. PCT/EP2006/002184, filed on Mar. 9, 2006.

(30) Foreign Application Priority Data

Apr. 8, 2005 (EP) ..................................... 05007787

(51) Int. Cl.
| | |
|---|---|
| *A61B 17/34* | (2006.01) |
| *A61B 5/145* | (2006.01) |
| *A61B 5/1473* | (2006.01) |
| *A61B 5/1486* | (2006.01) |
| *A61B 5/00* | (2006.01) |

(52) U.S. Cl.
CPC ...... *A61B 17/3468* (2013.01); *A61B 5/14532* (2013.01); *A61B 5/1473* (2013.01); *A61B 5/14865* (2013.01); *A61B 5/6849* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,966,551 | A * | 10/1990 | Betush | ........................... 433/95 |
| 5,299,571 | A | 4/1994 | Mastrititari | |
| 5,390,671 | A * | 2/1995 | Lord | .................. A61B 5/14865 204/403.01 |
| 6,275,717 | B1 * | 8/2001 | Gross | ................. A61B 5/14865 600/309 |
| 6,560,471 | B1 * | 5/2003 | Heller | .................. A61B 5/0002 600/309 |
| 6,695,860 | B1 * | 2/2004 | Ward | ....................... A61B 5/00 600/505 |
| 2002/0022855 | A1 * | 2/2002 | Bobroff et al. | ............... 606/185 |
| 2004/0133164 | A1 * | 7/2004 | Funderburk | ....... A61B 5/14532 604/134 |
| 2004/0138543 | A1 | 7/2004 | Russell et al. | |
| 2007/0197889 | A1 * | 8/2007 | Brister et al. | ................. 600/347 |
| 2008/0097246 | A1 * | 4/2008 | Stafford | ....................... 600/584 |
| 2012/0190951 | A1 * | 7/2012 | Curry | ................. A61B 5/14503 600/345 |
| 2012/0303043 | A1 * | 11/2012 | Donnay | ............... A61B 5/6849 606/129 |

* cited by examiner

*Primary Examiner* — Christian Jang
*Assistant Examiner* — Karen E Toth
(74) *Attorney, Agent, or Firm* — Bose McKinney & Evans LLP

(57) ABSTRACT

A device for positioning a probe in living tissue, the device including a casing having an underside for positioning on the tissue, the probe, which can be moved relative to the casing beyond the underside in an insertion direction to be inserted into the tissue, and a signal means carried by the casing such that it can be moved in the insertion direction to an end position, wherein the signal means slaves the probe when moving in the insertion direction.

26 Claims, 3 Drawing Sheets

DEVICE FOR POSITIONING A PROBE IN LIVING TISSUE

CROSS-REFERENCE TO RELATED APPLICATIONS

This application is a continuation of International Application No. PCT/EP2006/002184 filed on Mar. 9, 2006, which claims priority to European Application No. EP 05 007 787.4 filed on Apr. 8, 2005, the contents of both of which are incorporated in their entirety herein by reference.

BACKGROUND

The present invention relates to devices for administering, delivering, dispensing, injecting or infusing a substance, and to methods of making and using such devices. More particularly, the present invention relates to a device for positioning a probe in vivo. The probe can be a measuring probe for ascertaining, e.g. continuously ascertaining, the value of one or more parameters which characterize(s) the state of health of an organism. In some embodiments, the device may be used for measuring, testing, sensing and/or communicating purposes in therapies such as, for example, diabetes therapy, in which a user administers a medicine, for example insulin, to him/herself and also positions the probe and evaluates information or a reading from the device him/herself.

A device for positioning a measuring probe in vivo is known from U.S. Pat. No. 6,695,860 B1, the probe comprising an ex vivo portion which remains on the skin at the positioning location, the measuring probe being the in vivo portion. The measuring probe is positioned in the tissue by an injection needle. Once the probe has been positioned, the injection needle is separated from the measuring probe and automatically moved back into the ex vivo portion of the device. A signal means is accommodated in the device and communicates with the measuring probe in a way which is not described.

SUMMARY

It is an object of the present invention to provide a device comprising a probe which can be positioned in living tissue, the device enabling the probe to be positioned in vivo and enabling communication with, e.g., to and/or from, the probe in a reliable, but simple and therefore inexpensive way.

In one embodiment, the present invention comprises a device for positioning a probe in living tissue, the device comprising a casing having an underside for positioning on the tissue, the probe, which can be moved relative to the casing beyond the underside in an insertion direction to be inserted into the tissue, and a signal means carried by the casing such that it can be moved in the insertion direction to an end position, wherein the signal means slaves the probe when moving in the insertion direction.

In some embodiments, the present invention comprises a device for positioning a probe in living tissue, the device comprising a casing having an underside for contacting the tissue, the probe, which is moveable relative to the casing beyond the underside in an insertion direction to be inserted into the tissue, and a signal device or mechanism carried by the casing such that it can be moved in the insertion direction to an end position. In some embodiments, the signal device slaves the probe when moving in the insertion direction. The signal device may comprise any mechanical, electrical, electro-mechanical, analog or digital mechanism or device suitable for generating, processing, sensing, conveying and/or communicating a time varying quantity, e.g., information, chemical or biochemical characteristics, data, messages, protocols, events, etc. In some embodiments, the device of the present invention further comprises an insertion aid for the probe.

In some embodiments, the present invention relates to a device for positioning a probe in a living tissue, the device comprising a casing having an underside which can be positioned on the tissue, the probe and a signal means for the probe. When the device is in use, the probe is an in vivo part, while the casing and the signal means remain on the tissue, i.e. ex vivo, at the positioning location. To remain on the tissue, the casing is provided with one or more fasteners, by which it can be fastened, e.g. adhesively, on the tissue. For instance, the underside of the casing can be provided with an adhesive pad or a directly applied adhesive agent. The probe can be moved relative to the casing, beyond the underside of the casing in an insertion direction, to be inserted into the tissue. The insertion direction can point at right angles to the underside, i.e. to the upper side of the tissue. Instead, however, it can also point at an inclination, e.g. a constant inclination, to the underside. The signal means serves to transmit and/or process signals from or for the probe. The exchange of signals can be bidirectional, but, in some embodiments, is unidirectional from the probe to the signal means. If the probe has to be supplied with power in order to operate, this power may be transmitted from the signal means to the probe. To this end, the signal means can be equipped with a power source or can itself serve merely to channel power from another power source, e.g. accommodated by the casing.

In accordance with the present invention, the probe can be inserted into the tissue using the signal means. To fulfil this additional function, the casing mounts or carries the signal means such that it can be moved in the insertion direction to an end position. The signal means is coupled to the probe such that it slaves the probe during its own movement in the insertion direction. When the signal means assumes its end position, the probe is positioned in the tissue, with the casing lying on the tissue at the location provided for.

Due to the double function of the signal means, namely as signal means and insertion means, a simple design is achieved for the device. Since the signal means simply slaves the probe during its movement in the insertion direction, the probe can retain its position relative to the signal means during the entire insertion movement. Although the possibility is not to be excluded that communication between the probe and the signal means is achieved wirelessly or by a wire connection via a sliding contact, in some embodiments the invention does however advantageously enable the probe and the signal means to be connected to each other via a continuous, fixed signal wire which is mechanically uninterrupted and which is fixedly connected to the signal means on the one hand and the probe on the other. This enables a transmission of signals which is both reliable in terms of signalling and resistant to mechanical disruption. If the probe is also supplied with power by or via the signal means, the same applies to the transmission of power—which is then achieved by a wire connection—wherein the signal wire can in a second function simultaneously also provide for the transmission of power, or a separate connecting wire can be provided for the transmission of power. In some embodiments, at least one signal wire is fixed on or in a connecting structure which rigidly connects the probe to the signal means.

In order to achieve an advantageously simple mechanical construction for the device and a simple and reliable transmission of signals, it would admittedly be conceivable in principle for the signal means to slave the probe in the insertion direction simply by pressing loosely against the probe. However, if—as is preferred in some embodiments—the probe and the signal means are fixedly connected, then they are connected to each such that they cannot move in and counter to the insertion direction. In some preferred embodiments, they are connected to each other rigidly, i.e. such that they cannot move relative to each other in any respect.

In a preferred embodiment, the casing guides the signal means in a guiding contact along a guiding path extending in the insertion direction, i.e. the casing and the signal means or a carrier part for the signal means form a cam gear, e.g. a sliding joint, wherein one of the casing on the one hand and the signal means or carrier part on the other forms the guiding path, and the other forms the engaging member. It would however also alternatively be conceivable for the casing and the signal means to be coupled to each other in another way. Instead of a purely translational movement, or a purely linear movement, the insertion movement of the signal means could, for example, also be a pivoting movement and the signal means correspondingly coupled to the casing by a pivoting mechanism.

The probe can be formed as an injection means which can penetrate the surface of a tissue, e.g. the human skin. To this end, however, it would have to be formed to be correspondingly pointed and resistant to buckling. In some preferred embodiments, the device comprises an insertion aid for the probe which protects the probe as it is inserted into the tissue. A protective function can in principle be fulfilled if the insertion aid stabilizes the probe against bending or buckling as it is inserted. It would be sufficient for this if the insertion aid protruded into the probe in the insertion direction or was arranged next to the probe and overlapped it in the insertion direction to at least close to its distal end. In some preferred embodiments, the insertion aid features a cladding structure which protectively surrounds the probe, at least substantially and to at least close to its distal end. The cladding structure forms an injection needle which protrudes beyond the probe in the insertion direction and forms a needle tip at its distal end. A cladding structure can form the injection needle. If an insertion aid is provided, the probe can advantageously be flexible, at least in sections, such that when it is in use, it does not cause irritation or at least causes less irritation than a probe which is rigid over its entire length, when for example a force is exerted on the casing, transverse to the surface of the tissue. Once the probe has been inserted, the insertion aid is drawn back out of the tissue, i.e. it can be separated from the probe or at least a part of the probe protruding into the tissue.

For co-operating with an insertion aid, it is advantageous for the probe to exhibit a free proximal end and a surface which is continuously free, i.e. accessible, from the proximal end to at least close to its distal end, thus enabling a protective, stabilizing overlap by the insertion aid. For stabilizing, the insertion aid should contact the probe in its overlap. In some embodiments, the probe and the insertion aid contact each other two-dimensionally over the free surface of the probe.

If an injection needle is provided for inserting the probe, such an insertion aid forms a needle protection to protect the user from pricking injuries from the injection needle once it has been separated from the probe. To this end, a preferred embodiment of the insertion aid comprises two pivoting blades which can be pivoted towards each other from an extended state, which the insertion aid assumes for inserting the probe, into a protective state. In the protective state, the pivoting blades lie substantially along the injection needle and shield its tip from the outside. The pivoting blades can be rod-shaped. In some preferred embodiments, they are lamina-shaped or curved to reliably shield the needle tip from being accessed not only from the front but also laterally.

In some preferred embodiments, the signal means is mounted on a carrier part; e.g., it is embedded in the carrier part. The casing mounts the carrier part such that it can be moved, in sliding contact, in the insertion direction up to the end position. In preferred embodiments, the device is in two parts and consists of the casing which serves to position and fix the device on the surface of the tissue, and the carrier part which carries the signal means. The insertion aid is provided for inserting the probe, and in such embodiments is also added as a third part, but is removed once the probe has been positioned, such that while the probe is in operation, the device is only in two parts, i.e. comprises two parts which can be moved relative to each other. However, the casing and the carrier part form a unit in the sense that when they are in use, e.g. when positioning the probe and while it is in operation once positioned, they are fixedly connected to each other—aside from the mobility of the carrier part relative to the casing as is required for positioning—and can be handled as a unit, such that positioning the casing on the surface of the tissue also simultaneously positions the carrier part, which then merely has to be moved from an initial position, relative to the casing, into the end position. In its initial position, the carrier part is advantageously fixed to the casing. However, the fixation is releasable, so that the carrier part can be moved in the insertion direction. In some preferred embodiments, the fixation is automatically released when a force is exerted which acts on the carrier part in the insertion direction. The fixation can, for example, be established in a positive or non-positive lock by a releasable locking engagement, or in a purely frictional lock via frictional areas or even in a material lock, wherein in the latter case, the connecting stay or stays establishing the material lock is/are destroyed by exerting a force which acts on the carrier part in the insertion direction. In some embodiments, the carrier part is also fixed to the casing in its end position; it automatically fixes to the casing when it reaches the end position. The fixation in the end position can be releasable or non-releasable. It can be formed in a positive and non-positive lock by locking the carrier part to the casing, or again also in a purely frictional lock. The fixation in the end position is advantageously at least firm enough that the carrier part, when it is in use, cannot be inadvertently moved relative to the casing, counter to the insertion direction.

In some embodiments, the carrier part also holds the probe and thus also forms a probe holder in such embodiments. The probe is advantageously connected to the carrier part such that it is accessible in the insertion direction from a side facing away from the underside of the casing, from an upper side of the carrier part opposite the underside of the casing. This accessibility is advantageous when the device comprises the insertion aid cited, since the insertion aid can then be very easily removed from the probe and the carrier part, counter to the insertion direction. To this end, the probe can be arranged on a side wall, on an outer circumference of the carrier part, or in a cavity or breach in the carrier part, and fastened to the carrier part. To this end, in some preferred embodiments, the carrier part is provided with a central breach which points in the insertion direction. The probe extends from a region of the breach which is central in relation to the cross-section, beyond the carrier part in the insertion direction.

In principle, the probe can already protrude beyond the underside of the casing when the carrier part is in its initial position, however in some preferred embodiments, it is short of the underside, such that it is protected by a base of the casing forming the underside. If the device features an insertion aid, then in a storage state in which the device can be stored before it is used, said insertion aid can form an additional protection for the probe on the side of the device facing away from the insertion direction. The probe can thus be accommodated, e.g. encapsulated, in a hollow space formed between the casing and the carrier part for the mobility of the carrier part.

The probe can be provided for positioning in muscular tissue or for example in a vein. In some preferred embodiments, it is for positioning under the skin, i.e. in subcutaneous tissue, or as applicable in the skin. It can serve to supply a product fluid to be administered, and in such an embodiment can form a catheter head which is connected to an infusion apparatus via a catheter. In a preferred embodiment, the probe is embodied as a measuring probe and is used to ascertain—e.g. continuously over a number of hours or days—a parameter, e.g. a biochemical parameter, which characterizes the state of health of the organism. Such a measuring probe can operate according to a method based on an exchange of material, and in such embodiments can, for example, be formed as an enzymatic sensor or viscosimetric affinity sensor. Enzymatic sensors and viscosimetric affinity sensors are suitable for determining the concentration of glucose. In alternative embodiments, however, the measuring probe can also operate according to other methods not including the transport of material in or out of or through the probe, for example as an infrared probe. The types of probe explicitly cited are to be understood as examples; in principle, the probe can, for example, be a temperature sensor or can comprise electrodes for measuring resistance. The probe can also be equipped with a combination of a number of types of sensor, e.g. a number of the types of sensors cited. In a preferred application, it is used to continuously monitor one or more parameters. In some embodiments, it can also be a combination of a measuring probe and a probe for administering a product fluid, wherein the measuring part of such a combined probe advantageously ascertains a parameter which is crucial to administering the product fluid, to be able to regulate the supply rate of the product fluid in a closed loop or at least control the supply rate of the product fluid on the basis of the ascertained values by a user intervention on an administering apparatus.

In some embodiments, the signal means can be formed purely as a channeling means which relays signals received from the probe to a processing unit, for example an infusion apparatus carried by the user or a handheld computer and/or PDA, PC, laptop or comparable data terminal. To enable data to be relayed wirelessly, such a signal means may be equipped with a transmitter, e.g. a radio transmitter. To relay the signals received, the signal means can also feature a signal memory, e.g. a digital data memory. If a memory is provided, then relaying the signals wirelessly or by a wire connection to a processing means can in principle be omitted, namely if the signals do not have to be evaluated concurrently. In such a case, the signal means or just its memory can be connected to the processing means for the purposes of evaluation, e.g. via a standard port, for instance a USB port, after the device has been used. In preferred embodiments, however, the signal means itself forms a processing means for the signals received. In such embodiments, the signal means is also capable of communicating with another processing means which forms an administering apparatus, for example an infusion pump, or a handheld and/or PDA, PC or laptop. In such embodiments, the signal means likewise communicates wirelessly, e.g. by radio, or as applicable by a wire connection to the other processing means. The device can be equipped with an optical and/or acoustic and/or tactile display, to display the readings or parameter values derived from them by the signal means, also for example by an acoustic and/or tactile alarm signal, for example a vibration signal.

In some embodiments, the device may be used in combination with an administering apparatus which the user of the device carries on his/her body constantly or at least over long periods of time, for administering. The administering apparatus and the device are adapted to each other for communication. Said communication can be bidirectional, but in some embodiments is unidirectional, wherein the administering apparatus receives signals from the device, e.g. by radio. The signals—e.g. readings already prepared by the signal means or as applicable parameter values already derived from them—are transmitted to the administering apparatus and further processed by its processing means if required. The readings or the parameter values derived from them are displayed on the administering apparatus, e.g. optically or, if critical states are determined, also in the form of an acoustic and/or tactile alarm signal. The administering apparatus can display the readings or the parameter values derived from them constantly or only when requested by the user. The device can also be supplied together with a specifically adapted, separate display apparatus which can be conveniently carried in a pocket and communicates with the signal means via radio. The display apparatus features a processing means of its own for processing the signals received from the signal means. The separate display apparatus can be a commercially available handheld computer and/or PDA or comparable apparatus which communicates with the signal means via a standard interface, for example Bluetooth. The signal means is fitted with a corresponding standard interface, for example a Bluetooth transmitter and/or receiver. If the device is supplied in combination with an administering apparatus, the same advantageously applies.

With respect to its power supply, in some embodiments, the device is autarkic, i.e. it is itself fitted with a power source, e.g. a battery. The carrier part cited advantageously also mounts the power source.

DETAILED DESCRIPTION

Figure 1:
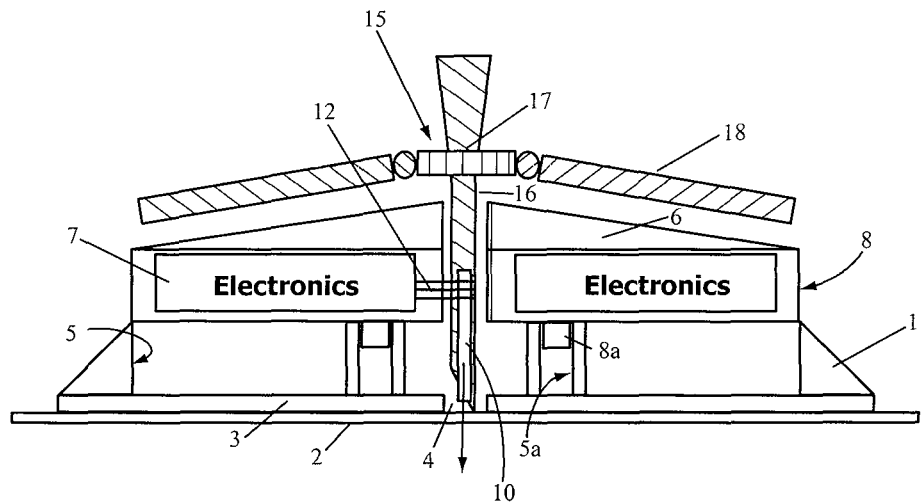
FIG. 1 depicts one embodiment of a device for positioning a probe in living tissue in accordance with the present invention.

FIG. 1 shows a device for positioning a probe in living tissue, e.g. in the human body, in a longitudinal section. The device comprises a casing 1 with an underside 2 for positioning and fastening the device on the surface of the tissue, e.g. the skin. The device further comprises a signal means 7 and a carrier part 6 which carries both the signal means 7 and the probe 10. The signal means 7 is embedded into the carrier part 6, and the probe 10 is rigidly connected to the carrier part 6. The probe 10 is connected in terms of signalling to the signal means 7 via the rigid connection, by a number of signal wires 12. The probe 10 is formed as a measuring probe for subcutaneous positioning and for measuring a parameter which characterises the state of health of an organism, e.g. a human being. The device of the exemplary embodiment serves to continuously monitor the glucose concentration in the subcutaneous tissue. Correspondingly, the probe 10 forms a glucose sensor. It should be understood that the signal means or device may comprise any mechanical, electrical, electro-mechanical, analog or digital mechanism or device, and/or a housing or carrying structure, suitable for generating, processing, sensing, conveying and/or communicating a time varying quantity, e.g., information, chemical or bio-chemical characteristics, data, messages, protocols, events, etc.

In one embodiment, the signal means 7 is formed as an electronic signal processing means. It receives measurement signals, e.g. electronic measurement signals, from the probe 10 via the signal wires 12. In alternative embodiments, the signal wires 12 can also be formed by a material supply to the probe 10 and a material drain from the probe 10, if the probe 10 is, for example, formed as a viscosimetric affinity sensor, and the signal means 7 evaluates a liquid enriched with glucose and channeled through the probe 10, in a way which is known in its own right. If the probe 10 is formed as a viscosimetric affinity sensor, signals are however still derived in the probe 10, and the measurement signals from the probe 10 are electronically or as applicable optically transmitted to the signal means 7 via the signal wires 12.

When the device is in its storage state as shown in FIG. 1, the carrier part 6 assumes an initial position relative to the casing 1 and is releasably locked to the casing 1 in the initial position. The probe 10 is rod-shaped and exhibits a longitudinal axis L. The carrier part 6 can be linearly moved relative to the casing 1, in an insertion direction V along the longitudinal axis L, from the initial position assumed in FIG. 1 to an end position.

During said movement, the casing 1 guides the carrier part 6 in a guiding contact. The guiding contact is formed as a sliding contact between a guiding path 5 of the casing 1 and a guiding path 8 of the carrier part 6. An inner surface area of the casing 1 forms the guiding path 5 and an outer surface area of the carrier part 6 forms the guiding path 8. The carrier part 6 is further connected to the casing 1, secured against rotation, to which end the casing 1 is provided with engaging elements 5a and the carrier part 6 is provided with engaging elements 8a.

The casing 1 comprises a disc-shaped, flat base 3, the underside of which has an adhesive pad attached to it which forms the underside 2 of the casing 1. Instead of an additional adhesive pad, the base 3 could also directly form the underside of the casing 1 and, to this end, can itself be provided for example with an adhesive agent. The base 3 comprises a central breach or opening 4. A casing wall comprising an inner surface area which is parallel to the insertion direction V projects from the base 3 on the upper side of the base 3 facing away from the underside 2, encircling the breach 4, e.g. cylindrically, to form the guiding path 5 of the casing 1. Correspondingly, the guiding path 8 of the carrier part 6 is likewise parallel to the insertion direction V. The casing 1 and the carrier part 6 form a sliding joint with the guiding paths 5 and 8 as a guiding cam and engaging member. The guiding paths 5 and 8 each extend over the entire length of the mobility of the carrier part 6. In principle, however, it would be sufficient for only one of the guiding paths 5 and 8 to extend over the entire length and for the other to only extend over a portion of the length.

The probe 10 is attached to the carrier part 6 such that its longitudinal axis L points in the insertion direction V. The carrier part 6 is likewise provided with a breach or opening, flush with the breach 4 along the longitudinal axis L, in which the probe 10 is fastened, pointing in the insertion direction V. The probe 10 is arranged centrally in the breach in the carrier part 6 with respect to the cross-section of the breach and is mechanically connected to the carrier structure 6 by a lateral connecting stay. The signal wires 12 are fixed in or on the connecting stay. In this way, the probe 10 and the signal means 7 are rigidly connected to each other. In particular, a signalling connection which is not altered permanently exists via the signal wires 12.

In the storage state shown in FIG. 1, the casing 1 and the carrier part 6 enclose a hollow space. The probe 10 protrudes out of the breach in the carrier part 6 into the hollow space, wherein its distal end lies opposite the breach 4 in the casing 1, wherein the distal end of the probe 10 protrudes into the breach 4. In the storage state, however, the breach 4 is sealed by the adhesive pad.

In the storage state, the device further comprises an insertion aid 15 which protects the probe 10 as it is inserted into the tissue. The protection consists substantially of stabilizing the probe 10 against bending or buckling. The insertion aid 15 comprises a cladding structure 16 which, when the device is in its storage state, protrudes or extends through the breach in the carrier part 6 to surround the probe 10. The cladding structure 16 is formed as an injection needle and is referred to as such in the following. It protrudes beyond the probe 10 in the insertion direction V, but is still likewise short of the adhesive pad. The distal end of the injection needle 16 is pointed. The insertion aid 15 further comprises a needle holder 17, from which the injection needle 16 projects, and a pivoting blade 18 on each of both sides of the injection needle 16. The pivoting blades 18 are connected to the needle holder 17, each by a pivot joint. They can be pivoted from a respectively pivoted position which they assume when the device is in its storage state, towards the injection needle 16, into a protective position. On its side facing away from the injection needle 16, the insertion aid 15 comprises a handle by which a user of the device can grip the insertion aid 15 and withdraw it from the probe 10 and carrier part 6, counter to the insertion direction V.

Figure 2:
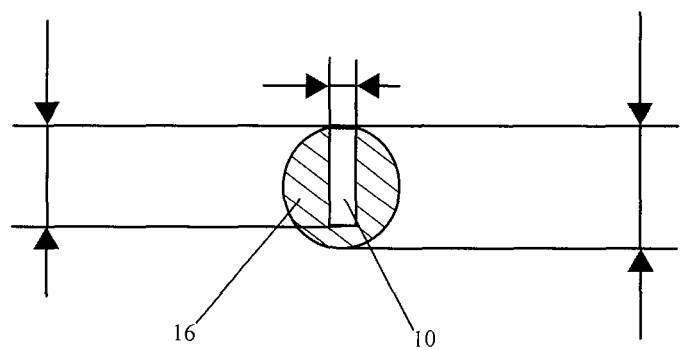
FIG. 2 depicts the probe and a cladding structure which protects the probe.

FIG. 2 shows the probe 10 and the injection needle 16 in cross-section. The injection needle 16 surrounds the probe 10 in a tight fit over almost its entire free surface. To the end, it exhibits a full cross-section which is provided with an accommodating slit for the probe 10. On one side, on which the probe is connected to the carrier part 6 transverse to the insertion direction V, the slit feeds onto the outer circumferential area of the injection needle 16. To be able to withdraw the injection needle 16 from the probe 10 once the probe 10 has been positioned in vivo, the slit extends up to the distal end of the injection needle 16.

The probe 10 protrudes beyond the carrier part 6 in the insertion direction V by a length which is suitable for subcutaneously positioning it. In some embodiments, the length protruding beyond the carrier part 6 should measure at least 4 mm and not exceed 12 mm. At least one of the guiding paths 5 and 8 is correspondingly or complementarily long and the hollow space remaining between the base 3 of the casing 1 and the carrier part 6 is correspondingly or complementarily dimensioned. In the end position, the carrier part 6 contacts the base 3 of the casing 1 directly. In the end position, it lies two-dimensionally on the base 3. In the end position, the carrier part 6 is advantageously fixed to the casing 1 firmly enough that the carrier part 6 cannot leave the end position due to the stresses to be expected when it is in normal use. The fixation can, for example, be formed as a locking engagement between the casing 1 and the carrier part 6 or a frictional lock between the guiding paths 5 and 8. To achieve a device which is as flat or thin as possible, as measured at right angles onto the underside, the base 3 of the casing 1 should be as thin as possible, which is also advantageous for equipping the underside of the casing 1 with a certain flexibility, such that it is not completely rigid but can adapt to a curvature of the surface of the tissue. A flat design is further accommodated if the casing 1 only projects from the upper side of the base 3, at right angles to the underside 2, as far as is required for guiding the carrier part 6 and fixing it in the initial position. The same also applies to the carrier part 6. If, as in the exemplary embodiment, the insertion direction V points at right angles to the underside 2, then once the insertion aid 15 has been removed and the carrier part 6 is situated in the end position, the device can have an overall height, as measured at right angles onto the underside 2, which roughly corresponds to the length by which the probe 10 protrudes beyond the bearing part 6 in the insertion direction V. The flat design is also accommodated if the insertion direction V points at right angles to the underside 2.

The following describes, with reference to FIGS. 1 and 3 to 6, a method of use, e.g., how the device is handled when positioning the probe 10 in vivo.

The user receives the device in the storage state shown in FIG. 1. The probe 10 is sterilely accommodated in the hollow space formed between the casing 1 and the carrier part 6. The carrier part 6 assumes its initial position. The insertion aid 15 lies on the upper side of the carrier part 6 or opposite this upper side at a slight distance, as shown in FIG. 1. In the storage state, the user takes the device in one hand and removes a cover on the underside 2 of the adhesive pad. The user then places the exposed adhesive area of the adhesive pad of the device onto the surface of the skin, over the desired measuring location. The device is then adhesively fixed on the surface of the skin via its underside 2. In the next step, the user presses the carrier part 6 in the insertion direction V up to the base 3, i.e. into the end position, relative to the casing 1. The injection needle 16 penetrates through the skin and into the subcutaneous tissue below. The insertion movement is generated by a manually applied pressure force acting on the carrier part 6 in the insertion direction V. The user exerts the pressure force by using the insertion aid 15, i.e. by the handle of the insertion aid 15. Due to the fixed connection between the carrier part 6 and the probe 10, the carrier part 6 slaves the probe 10 in its insertion movement. The injection needle 16 protects the probe 10 while it penetrates the skin and is subsequently inserted into the tissue below.

Figure 3:
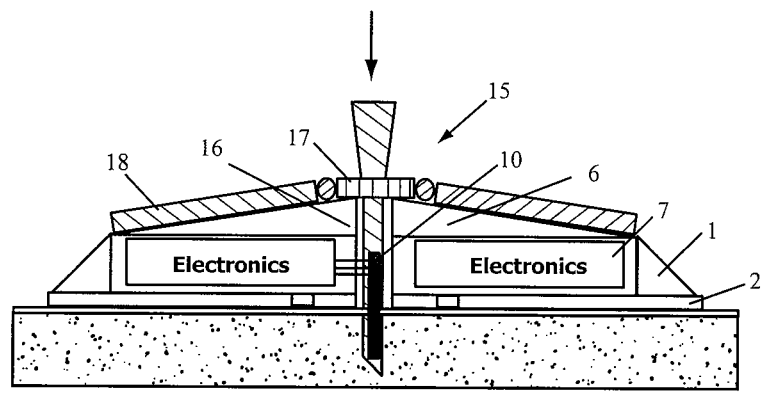
FIGS. 3 to 6 depict a sequence for positioning the probe in a tissue.

FIG. 3 shows the device after the probe 10 has been completely inserted, i.e. the carrier part 6 assumes the end position. The insertion aid 15 is still lying on the upper side of the carrier part 6.

Figure 4:
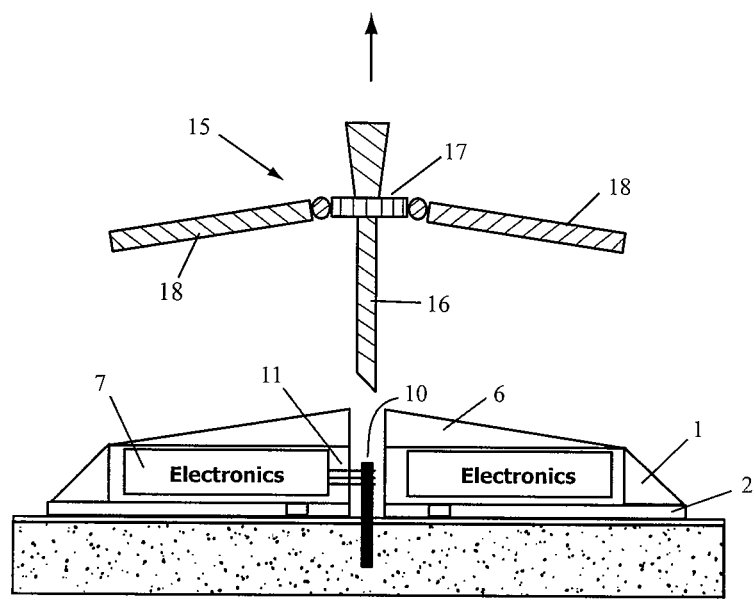

FIG. 4 shows the device after the insertion aid 15 has been separated from the probe 10 and also already separated from the carrier part 6. For separating, the user grips the insertion aid 15 by the handle and withdraws it linearly from the probe 10, counter to the insertion direction V, and removes it from the breach in the carrier part 6.

Figure 5:
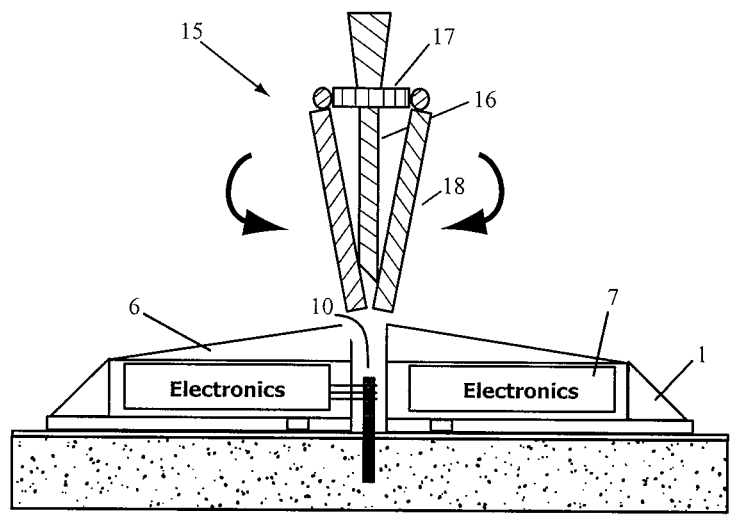

For secure handling and, for example, disposal of the insertion aid 15, the user pivots the pivoting blades 18 towards the injection needle 16 into the protective state shown in FIG. 5. In the protective state, the pivoting blades 18 can advantageously each assume a locking position or lock to each other, such that they cannot inadvertently leave the protective position. Alternatively or additionally, the two pivot joints can also be configured to be correspondingly stiff.

Figure 6:
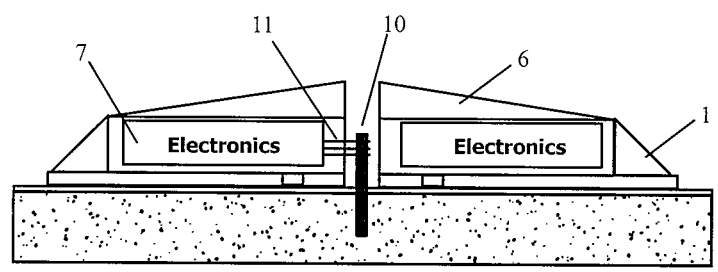

FIG. 6 shows the device in its operational state. The probe 10 continuously outputs measurement signals to the signal means 7, from which the current glucose concentration in the tissue can be ascertained.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for positioning a probe in living tissue, the device comprising:
    an insertion aid movable in an insertion direction and a retraction direction;
    a casing having an underside for positioning on the tissue;
    a probe that is movable relative to the casing beyond the underside in the insertion direction;
    an electronics unit slidably mounted to the casing, wherein the casing guides movement of the electronics unit in the insertion direction, and wherein the electronics unit has a transmitter, a signal memory and/or a processor; and
    a connector between the electronics unit and the probe, the connector mechanically and electrically connecting the electronics unit to the probe;
    wherein, during movement of the electronics unit in the insertion direction, a force is transmitted from the electronics unit through the connector to move the probe in the insertion direction to be inserted into the tissue, and wherein the probe remains fixed to the electronics unit when the insertion aid is moved in the retraction direction.

2. The device of claim 1, wherein the connector provides a rigid connection between the electronics unit and the probe.

3. The device of claim 1, wherein the connector comprises one or more signal wires.

4. The device of claim 1, wherein the electronics unit is housed in a carrier, the carrier having an opening in the insertion direction through which the probe protrudes when inserted in the tissue.

5. The device of claim 4, wherein the carrier cooperates with the casing during movement of the electronics unit in the insertion direction.

6. The device of claim 5, wherein the carrier and the casing form cooperating guiding paths.

7. The device of claim 1, further comprising an insertion aid for the probe, the insertion aid including a needle.

8. The device of claim 7, wherein the needle surrounds the probe and comprises a slit through which the connector extends to connect the probe to the electronics unit.

9. The device of claim 1, wherein the probe is a measuring probe for measuring a medical parameter in a body fluid.

10. The device of claim 1, wherein the electronics unit is positioned relative to the probe in a direction transverse to the insertion direction.

11. The device of claim 1, wherein the probe is fixed to the electronics unit.

12. A method of positioning a probe in living tissue, the method comprising:
provide a casing;
providing an electronics unit that is connected to the probe and is slidably mounted to the casing, the electronics unit having a transmitter, a signal memory and/or a processor;
mechanically and electrically connecting the electronics unit to the probe with a connector;
positioning an underside of the casing on the tissue;
using an insertion aid to move the electronics unit in an insertion direction, the electronics unit being guided by the casing; and
transmitting a force from the electronics unit through the connector to move the probe in the insertion direction into the tissue, whereby the probe is inserted into the tissue using the electronics unit;
wherein the probe remains fixed to the electronics unit after retraction of the insertion aid.

13. The method of claim 12, further comprising using the connector to communicate an electrical signal between the probe and the electronics unit.

14. The method of claim 12, further comprising defining the insertion depth of the probe as a function of the position of the electronics unit.

15. The method of claim 12, wherein the insertion depth of the probe is reached when the electronics unit is moved to an end position relative to the casing.

16. The method of claim 12, wherein the probe maintains the same position relative to the electronics unit during the movement of the electronics unit.

17. The method of claim 12, further comprising providing an insertion aid with a handle, depression of the handle moving the probe in the insertion direction, wherein the force is transmitted from the handle through the electronics unit to the probe.

18. The method of claim 17, further comprising positioning the electronics unit relative to the probe in a direction transverse to the insertion direction.

19. The method of claim 18, wherein the handle is depressed in the insertion direction.

20. The method of claim 12, wherein the probe maintains the same position relative to the electronics unit during the entire movement of the electronics unit.

21. The method of claim 12, further comprising establishing the final insertion depth of the probe as a function of the position of the electronics unit relative to the casing.

22. A device for positioning a probe in living tissue, the device comprising:
a casing having an underside for positioning on the tissue;
a probe that is movable relative to the casing beyond the underside in an insertion direction; and
an electronics unit slidably mounted to the casing, wherein the casing guides movement of the electronics unit in the insertion direction, wherein the electronics unit has a transmitter, a signal memory and/or a processor, and wherein the electronics unit is housed in a carrier having an opening in the insertion direction through which the probe protrudes when inserted in the tissue; and
a connector between the electronics unit and the probe, the connector mechanically and electrically connecting the electronics unit to the probe;
wherein, during movement of the electronics unit in the insertion direction, a force is transmitted from the electronics unit through the connector to move the probe in the insertion direction to be inserted into the tissue.

23. The device of claim 22, wherein the connector provides a rigid connection between the electronics unit and the probe.

24. The device of claim 22, wherein the connector comprises one or more signal wires.

25. The device of claim 22 wherein the carrier cooperates with the casing during movement of the electronics unit in the insertion direction.

26. The device of claim 25 wherein the carrier and the casing form cooperating guiding paths.

* * * * *